United States Patent [19]

Ritchie

[11] Patent Number: 5,596,948
[45] Date of Patent: Jan. 28, 1997

[54] ANIMAL URINE COLLECTION AND ANALYSIS SYSTEM AND ITS METHOD OF USE

[75] Inventor: David A. Ritchie, Crestwood, Mo.

[73] Assignee: Ralston Purina Company, St. Louis, Mo.

[21] Appl. No.: 492,380

[22] Filed: Jun. 19, 1995

[51] Int. Cl.⁶ ..................................................... A01K 1/03
[52] U.S. Cl. ........................... 119/417; 436/180; 128/771
[58] Field of Search ........................ 119/417, 421, 119/458, 479; 422/100, 82.03, 104; 436/180; 73/64.56; 128/771

[56] References Cited

U.S. PATENT DOCUMENTS

| | | | |
|---|---|---|---|
| 3,107,650 | 10/1963 | Cass | 119/417 |
| 3,228,375 | 1/1966 | Philippe | 119/417 |
| 3,460,395 | 8/1969 | Shaw | 128/771 X |
| 3,683,894 | 8/1972 | Villari | 128/771 X |
| 4,154,196 | 5/1979 | Gass | 119/417 |
| 4,181,612 | 1/1980 | Trail | 119/479 X |
| 4,341,017 | 12/1980 | Balistreri et al. | 128/771 X |
| 4,785,765 | 11/1988 | Campbell et al. | 119/417 |
| 5,015,591 | 5/1991 | Meyrat et al. | 436/180 |
| 5,183,765 | 2/1993 | Qureshi et al. | 436/180 |

*Primary Examiner*—Robert P. Swiatek
*Assistant Examiner*—Yvonne R. Abbott
*Attorney, Agent, or Firm*—Richard B. Taylor

[57] ABSTRACT

A system and method of using the system are provided for collecting and analyzing urine from an animal. A cage with a fluid pervious floor is provided for holding an animal. Urine from the animal flows through the cage floor into a hydrostatic column. An analyzing device is engaged with or positioned proximate to the column in position to analyze the urine entering the column. The column is structured to discharge a volume of liquid equivalent to the volume of urine that enters the column. The discharged liquid is received in a container which is located on a scale that weighs the received liquid. Data from the analyzing device and the scale is automatically stored by a data processing system. A rinse container with a liquid rinse is provided to rinse the column. Preferably the data processing system automatically controls valves to automatically rinse the column after each animal urination or after a predetermined period of time has elapsed.

40 Claims, 4 Drawing Sheets

ANIMAL URINE COLLECTION AND ANALYSIS SYSTEM AND ITS METHOD OF USE

BACKGROUND OF THE INVENTION

1. Field of the Invention

The present invention relates to the field of animal husbandry, and in particular to an apparatus and a method for collecting, and automatically analyzing urine from an animal over an extended period of time.

2. Description of the Related Art

Veterinarians and others involved in animal husbandry often analyze urine from an animal such as a cat or a dog to monitor the health of the animal. The urine is frequently measured for its pH, osmolarity, and other characteristics which can provide important information about the health of the animal. For example, the pH of a cat's urine may be related to the presence of feline urinary tract disease, a disease which afflicts significant numbers of cats. A single urine sample may be collected to make a spot check, or urine samples may be collected over a period of time from the animal to more accurately characterize the animal's health status.

Innovations for improving animal health may be developed by monitoring animal health through analysis of urine samples. For example, improved animal feed regimens may be developed from urine analysis health assessments of animals placed on specific feed regimens while the animals are on the feed regimens. Feed regimens which are found to improve the health of the animals may then be selected for further use.

Although analyzing animal urine is often a useful method for obtaining information about the health of the animal, urine collection has been difficult or has introduced impurities into the urine sample, while analysis has been time consuming and tedious. A commonly used method of obtaining a urine sample from an animal such as a dog or a cat has been to collect the sample directly from the animal's bladder. A needle is passed through the skin of the animal into the animal's bladder and urine is withdrawn from the bladder. This method of collecting urine, although effective, is invasive and causes the animal discomfort as well as creates a risk of injury to the animal. Furthermore, repeated urine collection from the bladder can increase the risk of bladder disease in the animal. In addition, each urine sample collected must be individually analyzed by a researcher, which may be quite time consuming if several animals are being tested to determine the effect of an innovation such as a feed regimen. Animal urine collection devices have been developed to provide a more convenient, safer way to collect urine from an animal. U.S. Pat. No. 4,869,206 to Spina provides an animal cage which permits collection of solid and liquid animal wastes for analysis. The animal cage has a perforated floor positioned over a sloped floor. Liquid waste from an animal in the cage passes through the perforated floor and is accumulated at the lowest point of the sloped floor where the waste is collected for analysis. U.S. Pat. No. 4,326,481 to Gruss provides an apparatus and procedure for collecting urine from cats. Flow through granular material is used as litter in a pan. Urine from a cat flows through the granular material and pools in the pan where it is collected for analysis.

These devices eliminate the need for invasive removal of urine from an animal but do not provide a fresh urine sample for analysis. Urine is accumulated in a pool in each of the devices to be collected at a later time for analysis. Pooled animal urine is quite susceptible to bacterial and/or chemical breakdown. Urine that has been bacterially or chemically altered may yield inaccurate analytical results, therefore a fresh urine sample is highly desirable. Furthermore, each urine sample collected from these devices must still be individually analyzed by a researcher.

Therefore, it is an object of the invention to provide an apparatus for collecting a urine sample from an animal and automatically analyzing the fresh urine sample.

SUMMARY OF THE INVENTION

The present invention provides an system and a method for analyzing animal urine. The system of the invention includes a cage for an animal, preferably a cat, from which urine is easily collected. The cage has a fluid pervious floor through which urine flows whenever the animal has a urinary event. The cage floor is fluidly coupled to a column so that urine flows through the cage floor to the column. The column has an inlet and an outlet with a U-shaped section between the inlet and outlet. The column is filled with liquid, which is maintained in hydrostatic equilibrium in the column with a trailing edge of the liquid proximate to the column inlet. As urine from the cage enters the column at the column inlet an equivalent volume of fluid is displaced from the column through the column outlet.

The urine in the column and the displaced liquid from the column are analyzed to provide information about the urine. An analyzing device or measuring means measures a characteristic of the urine. In one embodiment of the invention the analyzing device or measuring means is a meter having a probe for analyzing the ion content of the urine, most preferably the pH. The analyzing device or measuring means is located proximate to the inlet of the column to analyze the urine as the urine enters the column.

A weighing means is positioned to collect and weigh the liquid, either urine or a rinse fluid, discharged from the outlet of the column. The weighing means is preferably a container located on a scale where, most preferably, the container is free of any attachments so the container may be easily removed from the scale for emptying. The liquid discharged from the column is collected in the container. The scale weighs the liquid collected in the container. The rinse fluid is chosen to have a specific gravity approximately the same as the specific gravity of urine so that the weight of the discharged liquid, whether rinse or urine, is approximately equal to that of the collected urine.

In a favored embodiment, a data processing system is in data communication with the analyzing device to receive and store data about the urine from the analytical device. The data processing system is also in data communication with the weighing means to receive and store data from the weighing means to record the weight of urine from each urinary event and to determine the onset and the completion of a urinary event.

The column may be rinsed after each urinary event or after a predetermined period of time has elapsed. A rinse container containing a liquid rinse for rinsing the column may be fluidly coupled to the inlet of the column. A rinse controlling valve controls release of the liquid rinse from the rinse container to the column so that the column is rinsed only when desired. Preferably, a data processing system is connected to the rinse controlling valve to control operation of the valve to automatically rinse the column after a urinary event or after a predetermined period of time has elapsed.

In operation, an animal is located in the cage. When the animal urinates, the urine flows through the cage floor to the column inlet. As the urine enters the column an equivalent volume of liquid is discharged from the column outlet. The analyzing device analyzes the urine to determine a specified characteristic of the urine. The discharged liquid flows out of the column into the container. The scale weighs the liquid received in the container to determine the amount of urine excreted by the animal. Data from the analyzing device and from the scale is communicated to the data processing system where the data is stored.

After the animal urinates the column is rinsed with the liquid rinse. Preferably the rinse is automatically controlled by the data processing system. The data processing system determines that the urinary event and the analysis of the urine are complete and causes the rinse control valve to open so liquid rinse will flow from the rinse container into the column. The data processing system also closes a urine controlling valve which prevents urine from the cage from entering the column during the rinse cycle. The column is rinsed to remove the urine from the column. The liquid discharged from the column during the rinse is directed to a drain.

The urine collection analysis system and its method of use of the present invention are particularly useful for collecting and analyzing urine from one or several animals over an extended period of time. Each urination from a series of urinary events may be collected and analyzed for each animal without extensive monitoring or maintenance. The urine samples are collected with a minimum of risk and discomfort to the animals. The collected urine samples are immediately analyzed to prevent introduction of impurities that develop in pooled urine. Furthermore, the collected urine samples are automatically analyzed and the analytical data is automatically stored without using a researcher's valuable time.

DESCRIPTION OF THE PREFERRED EMBODIMENTS

Figure 1:
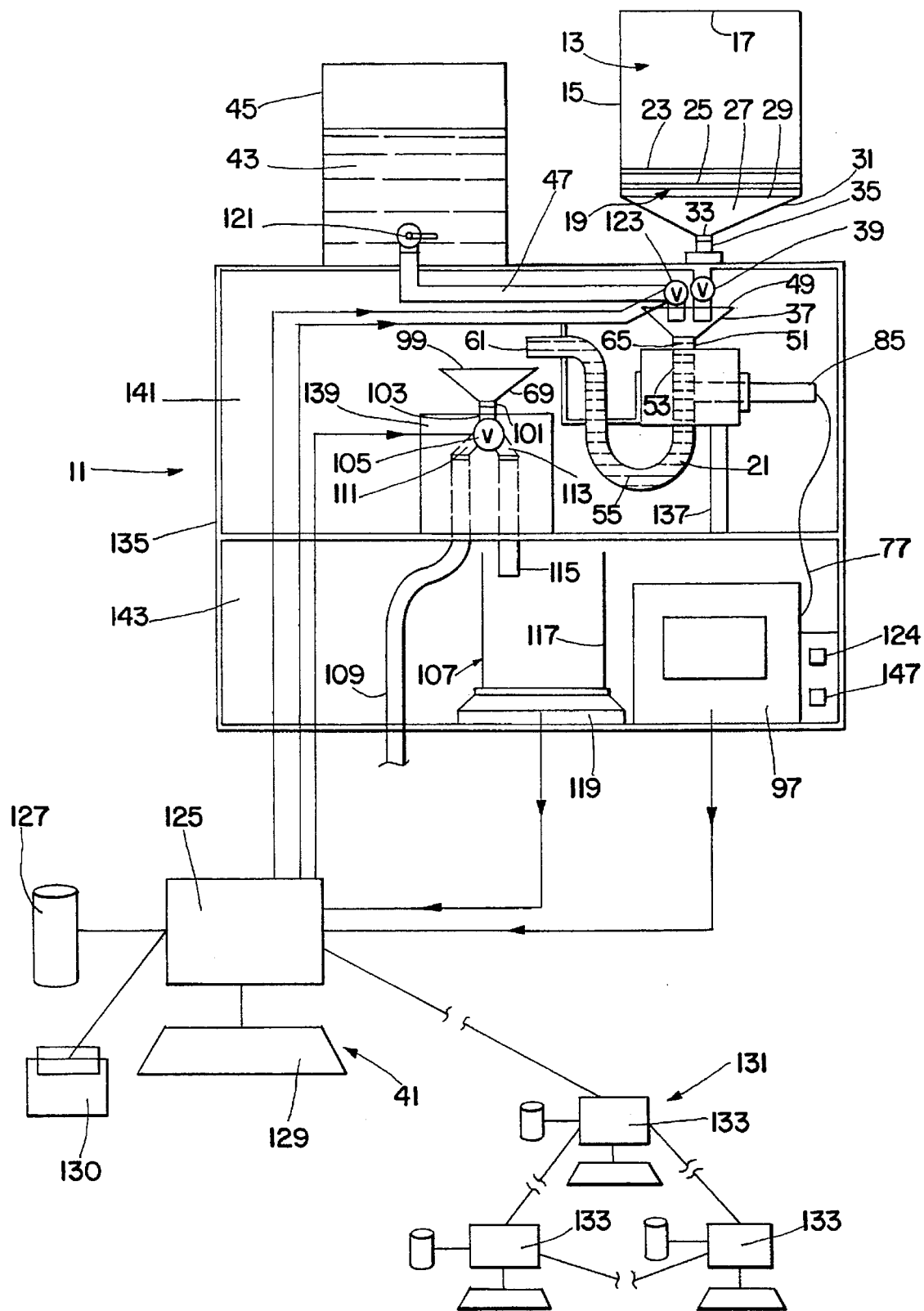
FIG. 1 is a schematic view of the system of the present invention.

The urine analysis system of the present invention is shown in FIG. 1, generally designated as 11. The system 11 automatically collects a series of urine samples from an animal, preferably a dog or a cat and most preferably a cat, and monitors specified physical characteristics of the collected samples. Preferably the physical characteristics to be monitored are indicative of an aspect of the animal's health. For example, the pH of a cat's urine may be monitored to detect the presence of feline urinary tract disease, a disease that is associated with a high pH urine.

Some of the characteristics that may be monitored by the system 11 include the ion content of each urine sample, preferably the pH, the weight of each urine sample, the total weight of the series of urine samples, and the date and time of each urinary event. Preferably, multiple cages are onitored simultaneously to determine these characteristics for a plurality of animals, where the cage and animal corresponding to a particular urinary event are recorded. The system 11 is not limited to monitoring these physical characteristics, and may be designed to measure other characteristics, for example the osmolarity of the samples. The urine samples are collected on a continuous basis flown the animal in a non-invasive manner and the collected samples are analyzed automatically by the system 11, minimizing or eliminating impurities that develop in stale urine samples and minimizing researcher effort required to analyze the samples. The system 11 is particularly useful for conducting long term tests to determine the health benefits of innovations to improve pet health, for example a feeding regimen to lower, and thereby improve, the pH of urine in cats.

Referring still to FIG. 1, the system 11 includes a cage 13 for holding an animal. The cage 13 has walls 15, a top 17, and a fluid pervious floor 19 which cooperatively hold the animal within the cage. The cage walls 15 and top 17 may be made of any conventional material used in constructing animal cages such as metal bars, or plastic.

The cage floor 19 is structured and arranged to support the animal while being pervious to fluids so that urine from the animal will drain from the cage floor to a hydrostatic column 21 where the urine is analyzed. The floor 19 is comprised of upper and lower mesh filter screens 23 and 25 and a tapered collection pan 27. The upper and lower mesh filter screens 23 and 25 extend between and couple the cage walls 15 near the bottom of the cage 13 with the upper mesh filter screen located directly over the lower mesh filter screen. The animal is supported in the cage 13 on the upper mesh filter screen 23. Urine from the animal passes through the upper and lower mesh filter screens 23 and 25 while the screens filter materials that would interfere with analysis of the urine such as feces, hair, and food particles. Preferably, the upper and lower mesh filter screens 23 and 25 are formed of stainless steel with standard mesh sizes of 2¾ and 20, respectively.

The tapered collection pan 27 is structured and arranged to collect and deliver urine from the cage 13 to tubing 35 which delivers the urine to the column 21. The collection pan 27 extends between and couples the lower ends of the cage walls 15 directly beneath the mesh filter screens 23 and 25. The collection pan 27 is funnel shaped, having a wide mouth 29, an inclined wall 31 and a drain port 33. The wide mouth 29 of the collection pan 27 is coupled to the cage walls 15. The inclined wall 31 extends from the cage walls 15 to the drain port 33, narrowing from the wide mouth 29 to the drain port. The drain port 33 is located centrally at the bottom of the collection pan 27 to receive and direct urine out of the pan.

Urine filtered by the mesh filter screens 23 and 25 flows into the collection pan 27, down the inclined wall 31, and out of the pan via the drain port 33. Preferably, the collection pan 27 is coated with a non-wetting material so that none of the urine remains in the collection pan. Most preferably the non-wetting material is polytetrafluoroethylene (Teflon).

Figure 5:
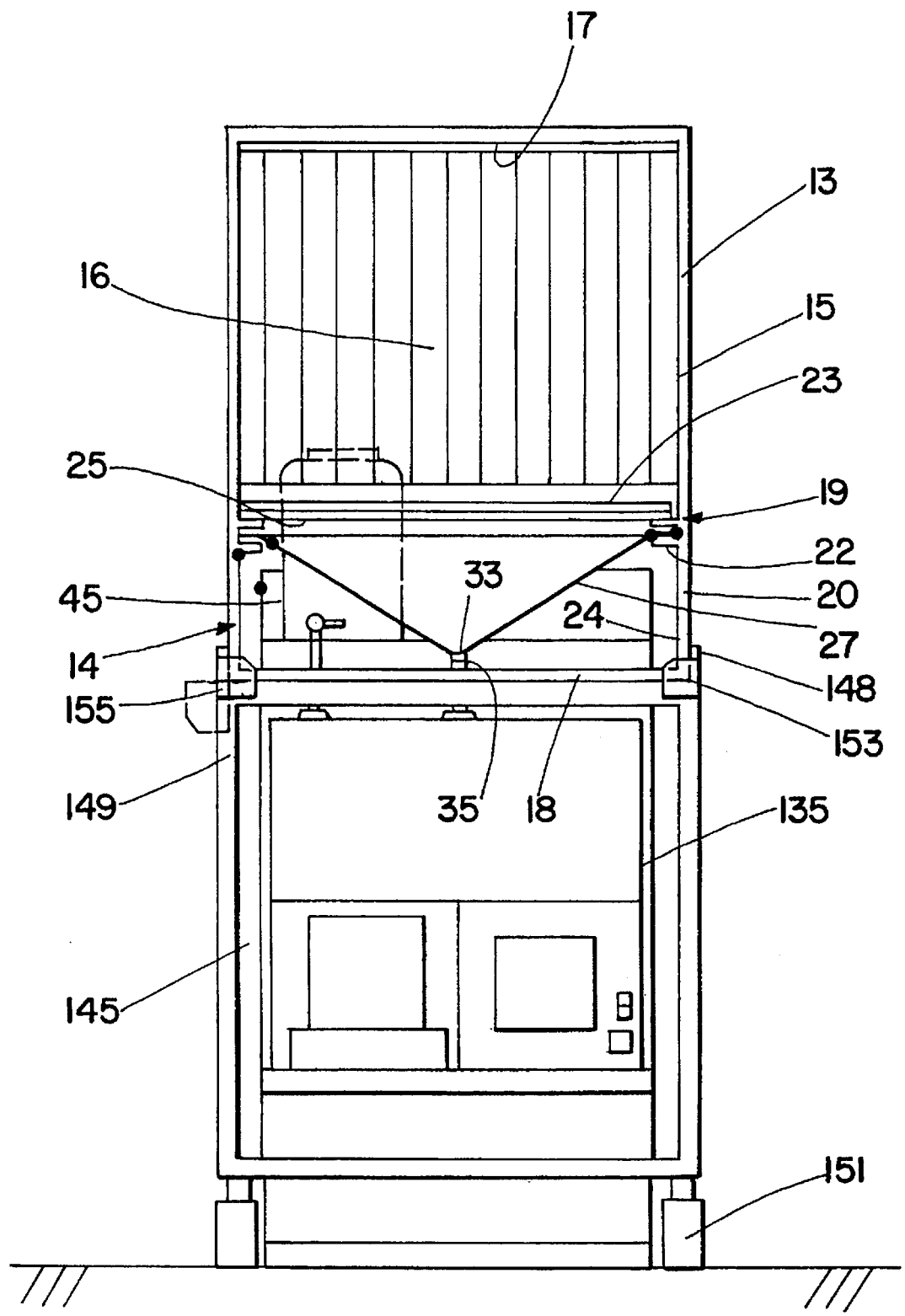
FIG. 5 is a front view of a frame for supporting the cage located about the housing of the system.

In a preferred embodiment, as shown in FIG. 5, the cage 13 includes a cage support frame 14 which supports an enclosure 16 formed by the cage walls 15, top 17 and floor 19. The cage support frame 14 has a base 18 with side braces 20 coupled to the base 18 extending transversely upward from the base. A support rail 22 integrally couples the inward face 24 of each side brace 20 opposing an opposite support rail 22. The collection pan 27 is supported in the cage support frame 14 in the support rails 22 and the mesh filter screens 23 and 25 and the cage walls 15 are supported in the frame 14 on the rails 22.

Referring back to FIG. 1, tubing 35 for delivering urine from the collection pan 27 to the column 21 couples the pan. The tubing 35 and the drain port 33 of the pan 27 are coupled in a fluid-tight relationship so that urine will flow from the drain port into the tubing without leaking. The tubing 35 extends downward from the pan 27 through a urine controlling valve 39 to a column inlet funnel 37 which directs urine into the column 21. Urine from the cage 13 flows by gravity from the pan 27 through the drain port 33 into the tubing 35 and through the tubing to the inlet funnel 37. Preferably the tubing 35 is formed of a non-wettable resilient material such as silicone rubber so that none of the urine remains on the walls of the tubing and the tubing can be easily pinched open and closed by the valve 39.

The urine controlling valve 39 is positioned to control flow of the urine through the tubing 35 from the cage 15 to the column 21. The urine controlling valve 39 is located along the tubing 35 between the pan 27 and the column 21 and is coupled to the tubing to control the flow of urine through the tubing. The valve 39 may be any type of conventional valve which is used for controlling liquid flow in tubing, but preferably the valve is a pinch valve which is normally open so urine may flow through the tubing 35 to the column 21. Most preferably the valve 39 is an electronically actuated pinch valve which is controlled by a data processing system 41, as described in further detail below.

The column inlet funnel 37 receives urine from the tubing 35 or a liquid rinse 43 from a rinse container 45 and directs the urine or rinse into the column 21. The tubing 35 from the pan 27 and tubing 47 from the rinse container 45 are directed into the mouth 49 of the funnel 37. The neck 51 of the funnel 37 is coupled to the inlet 53 of the column. Preferably, the neck 51 of the funnel 37 and the inlet 53 of the column 21 are threaded so the column and the funnel may be threadably coupled together. Urine or liquid rinse 43 is deposited in the funnel 37 near the funnel mouth 49 and flows by gravity down the funnel through the funnel neck 51 into the inlet 53 of the column 21. The trailing edge 65 of the liquid 55 is maintained in the neck 51 of the funnel 37 as described in further detail below. The funnel 37 may be any conventional type funnel formed of a non-wettable material, preferably polypropylene, so the urine or the rinse 43 does not remain on the funnel wall.

Figure 2:
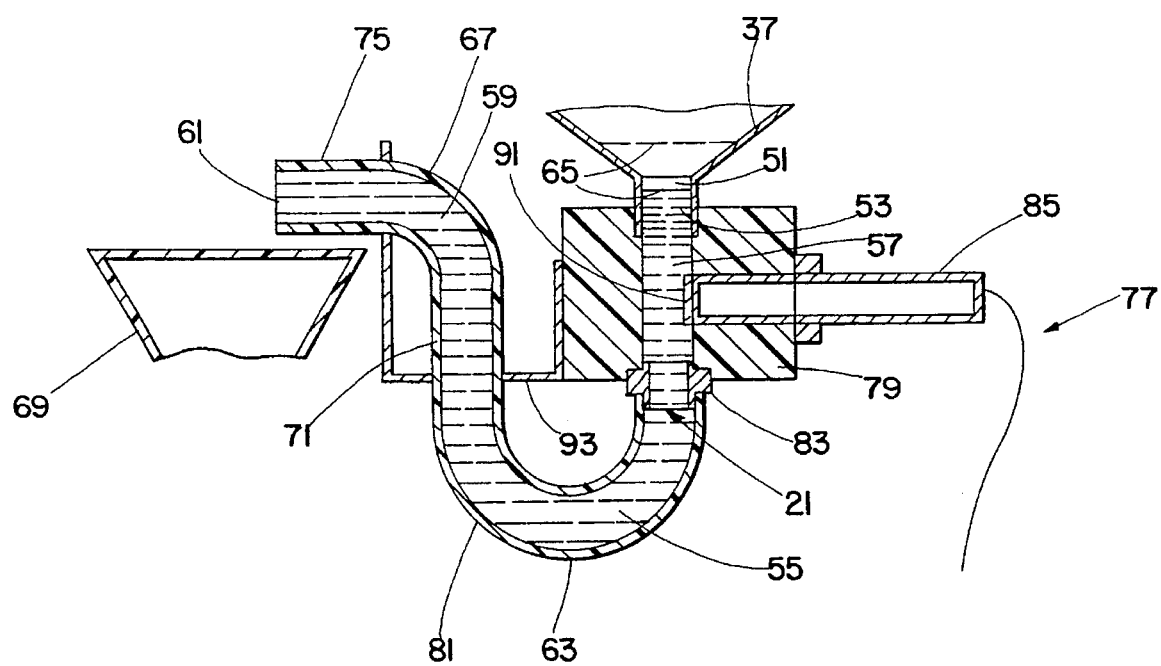
FIG. 2 is a side cross-sectional view of the column and the sensor probe of the system.

Referring now to FIG. 2, the column 21 is structured and arranged to receive urine from the animal in the cage through the funnel 37 and to discharge a volume of liquid corresponding to the volume of urine received from the animal. The column 21 is a hydrostatic column structured to contain a static volume of liquid 55. The column has an inlet section 57 which terminates in the column inlet 53, an outlet section 59 which terminates in the column outlet 61, and a U-shaped section 63 located between and coupling the inlet and outlet sections. Liquid 55 is trapped by gravity in the U-shaped section 63 and in the inlet and outlet sections 57 and 59 of the column 21.

The inlet section 57 is positioned to receive urine or liquid rinse 43 through the funnel 37. As described above, the column inlet 53 and funnel 37 are coupled together. Urine or rinse 43 enters the column 21 by gravity through the inlet 53 from the funnel 37. The column 21 is structured and arranged to maintain the trailing edge 65 of the liquid 55 proximate to the inlet 53 and directly above an analyzing device 77 so urine received in the column is positioned to be analyzed by the analyzing device or similar measuring means. The position of the outlet 61 relative to the column inlet 53 and the inlet funnel 37 determines the position of the trailing edge 65 of the liquid 55 since gravity maintains the column 21 in hydrostatic equilibrium with the trailing edge 65 of the liquid and the outlet 61 at an equal height. The outlet 61 is positioned to hold the trailing edge 65 of the liquid 55 in the neck 51 of the funnel 37 just above the column inlet 53 and the analyzing device 77. In a preferred embodiment, a bracket 93 holds the outlet section 59 of the column 21 with the outlet 61 in the desired position.

Added urine or rinse 43 displaces an equivalent volume of liquid 55 from the column 21 through the column outlet 61. As shown by the dashed line 65 in FIG. 2, urine or rinse added to the trailing edge of the liquid 55 in the neck 51 of the funnel 37 causes the volume of liquid in the neck 51 and funnel 37 to increase, raising the trailing edge 65 of the liquid relative to the position of the outlet 61. The increased volume of liquid disrupts the hydrostatic equilibrium of the column and creates a positive liquid pressure head which forces liquid 55 to flow through the column 21 and out of the outlet 61 until the trailing edge 65 is lowered to its initial position and the column regains hydrostatic equilibrium.

The outlet section 59 is structured to locate the outlet 61 over an outlet funnel 69 which collects the liquid discharged from the outlet. The outlet section 59 has an inner leg 71 and an outer leg 75 which are coupled together by a bended portion 67 of the outlet section. The inner leg 71 integrally couples the U-shaped section 63 of the column and extends vertically upwards to the bended portion 67. The outer leg 75 integrally couples the bended portion 67 and extends transverse to the inner leg 71 to the outlet 61 so the outlet is positioned over the outlet funnel 69.

Figure 3:
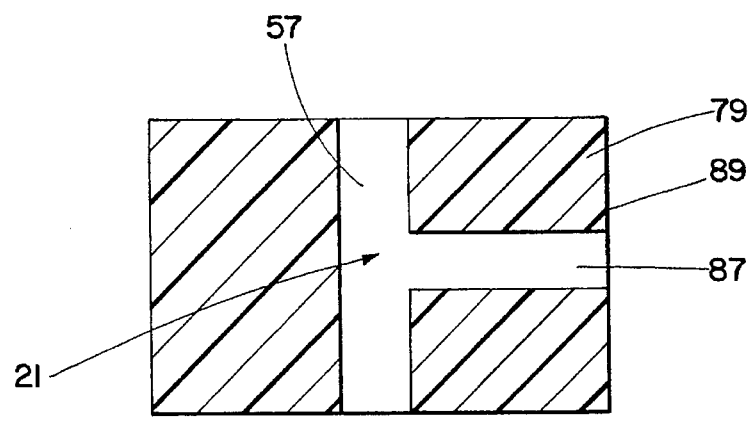
FIG. 3 is a side cross-sectional view of the sensor probe support block of the column.

In a preferred embodiment, as shown in FIG. 2, the column 21 is formed by a flow-through probe support block 79 and tubing 81 coupled together with a coupler 83. The two part column 21 is designed to permit a sensor probe 85 from the analyzing device 77 to be immersed in the liquid 55 in the column. The flow-through portion of the support block 79 forms the inlet section 57 of the column 21. As shown in FIG. 3, the support block 79 is preferably formed of a block of acrylic precision drilled to form the inlet section 57 of the column and a probe support aperture 87 that intersects the inlet section 57 and extends transversely from the column 21 to a side 89 of the support block. The probe support aperture 87 is sized so that the probe 85 will fit snugly in the aperture to prevent liquid from leaking about the probe 85 from the column 21 into the aperture. Referring back to FIG. 2, the support block 79 supports the probe 85 with a tip 91 of the probe extending into the liquid 55 in the column 21 near the column inlet 53 so the probe is positioned to analyze liquid entering the column.

Figure 4:
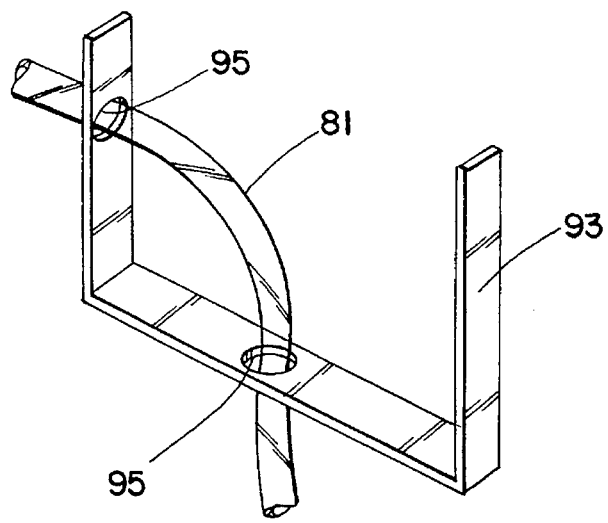
FIG. 4 is an isometric view of the tubing of the column supported in the support bracket.

Referring still to FIG. 2, the tubing 81 forms the U-shaped section 63 and the outlet section 59 of the column 21. The tubing 81 is secured in the desired position by the bracket 93 which is mounted to the support block 79. Preferably, as shown in FIG. 4, the tubing 81 is secured in the bracket 93 by being threaded through apertures 95 in the bracket 93. The tubing 81 is preferably flexible polyvinylchloride (Tygon) tubing.

Referring now to FIG. 1, the analyzing device 77 or measuring means is engaged with the column 21 or positioned adjacent to the column proximate to the column inlet 53. In a preferred embodiment, a probe 85 of the analyzing device 77 is engaged with or positioned adjacent to the column. The probe 85 is positioned just below the trailing edge 65 of the liquid 55 in the column so the probe can analyze urine from the animal as the urine enters the column. The probe 85 may extend into the column 21 to be immersed in the liquid 55 or may be located outside of the column depending on the characteristic being measured.

The analyzing device 77 or measuring means measures a selected characteristic of urine received in the column 21. Preferably, the analyzing device 77 comprises a conventional meter 97 for measuring the ion content of a liquid, and its probe 85. The meter 97 is typically used to measure the urine for ions which provide information about the health of an animal. Preferably the meter 97 measures the urine for sodium ($Na^+$), potassium ($K^+$), hydrogen ($H^+$), calcium ($Ca^{2+}$), magnesium ($Mg^{2+}$), chloride ($Cl^-$), or phosphorus ion content, however, measurement of the concentration of other ions is also contemplated. Most preferably the meter 97 measures the hydrogen ion content (pH) of the urine since the pH of cat urine can be modified to help reduce the formation of struvite crystals or uroliths often associated with feline lower urinary tract diseases. The meter probe 85 is a conventional probe for detecting a selected ion species. Preferably the probe 85 is a surface-type gel-filled electrode which is used in combination with a reference probe placed in a reference solution. Probes 85 may be interchanged as desired to measure the content of different ion species in the urine.

As urine is received and analyzed at the column inlet 53, a corresponding volume of liquid is discharged from the column outlet 61 into the outlet funnel 69. The outlet 61 of the column 21 is located over the mouth 99 of the outlet funnel 69 positioned so the entire volume of liquid discharged from the column is received into the funnel 69. The funnel 69 narrows to a funnel neck 101 which couples the inlet 103 of a three way valve 105 in a fluid-tight manner. Liquid from the column 21 flows by gravity out of the outlet 61 into the funnel 69 near the funnel mouth 99, down the funnel to the funnel neck 101, and out of the funnel neck into the three way valve 105. The funnel 69 may be any conventional type funnel formed of a non-wettable material, preferably polypropylene, so the liquid does not remain on the funnel wall.

The three way valve 105 directs the liquid into weighing means 107 for weighing the discharged liquid, or into a drain tube 109 which directs the liquid to a drain for disposing liquid waste. The three way valve 105 directs flow of liquid from the inlet 103 of the valve into either one or the other of two valve outlets 111 or 113. Outlet 111 is coupled to the drain tube 109 in a fluid tight manner so liquid may be directed from the funnel 69 to a drain. Outlet 113 is coupled in a fluid-tight manner to tubing 115 directed to the weighing means 107 so liquid may be directed from the funnel 69 to the weighing means. Outlet 113 to the weighing means 107 is usually maintained in an open condition by the valve 105 while outlet 111 to the drain is usually maintained in a closed position. Preferably, the three way valve 105 is a conventional pinch valve that alternatively pinches one of the outlets 111 or 113 closed while leaving the other outlet open. Most preferably the three way valve 105 is an electronically actuated pinch valve which is controlled by the data processing system 41, as described in further detail below.

Tubing 115 delivers liquid from the valve 105 to the weighing means 107. The tubing 115 extends downward from the valve 105 to the weighing means 107 so the liquid flows by gravity from the valve to the weighing means. Preferably the tubing 115 is formed of a non-wettable resilient material such as silicone rubber so the liquid does not stick to the walls of the tubing and the tubing can be pinched open and closed.

The weighing means 107 weighs the liquid to determine the weight of the urine received in the column. Preferably the weighing means is comprised of a container 117 and a scale 119. The container 117 receives and holds the liquid discharged from the column 21 by the addition of urine to the column. The container 117 is located on the scale 119, which weighs the liquid received in the container. The liquid 55 passing through the column 21 is either urine or liquid rinse 43. As noted above, the liquid rinse is chosen to have a specific gravity that is approximately equivalent to the specific gravity of urine so the volume of liquid received in the container 117 will have the same weight as the equivalent volume of urine which displaced the liquid from the column.

Preferably the container 117 is a conventional large beaker which is free of attachments so the container may be easily removed from the scale 119 for emptying. The tubing 115 is positioned over the container 117 so that the tubing may deposit liquid from the column 21 into the container but will not hinder removal of the container from the scale 119. Preferably the scale 119 includes a conventional autotracking feature so the scale will hold a previously measured liquid weight despite slow evaporation of the liquid from the container 117. The container 117 is open, not closed with the tubing 115 attached to an inlet of the container, since evaporation does not present a problem even when the weight of a series of urinations is to be measured over an extended period of time. The open container 117 may be easily removed from the scale 119.

The scale 119 measures the weight of the liquid displaced by the urine for each rinary event of a series of urinary events from the animal over the period of time the animal is held in the cage 13. The measured weight is automatically recorded, preferably by communicating the data to the data processing system 41 for processing and storage. The total weight of the series of urinary events is also measured by the scale 119 by combining and weighing the liquid displaced by each urination in the container 117. As described above, preferably the scale 119 has an autotracking feature so that evaporation of liquid from the container 117 does not reduce the total measured weight of the series of urinary events.

The system 11 includes a rinsing mechanism for rinsing the column 21 after each urination when the urine has been analyzed and weighed. Rinse container 45 contains liquid rinse 43 for rinsing the column 21. The rinse container 45 is fluidly coupled to the column by the tubing 47 so liquid rinse 43 from the container may flow from the container to the column 21. Preferably the rinse container 45 is a carboy with a nozzle 121 for coupling the tubing 47.

The liquid rinse 43 is preferably a conventional, commercially available pH buffer solution, most preferably having a pH of 4 or 7. A pH buffer solution is preferred since the solution can be used to rinse and stabilize the probe 85 of the analyzing device 77, which is immersed and maintained in the rinse 43 after the column is rinsed. The rinse 43 also is selected to have a specific gravity that is approximately the same as the specific gravity of urine since the rinse is used as the liquid 55 in the column, which is required to have an equivalent specific gravity to that of the urine as described above.

Tubing 47 couples the nozzle 121 of the rinse container 45 for delivering the liquid rinse 43 from the container 45 to the inlet funnel 37 and thence to the column 21. The tubing 47 and the nozzle 121 are coupled in a fluid-tight relationship to deliver the rinse 43 to the column without leaking. The tubing is positioned to deliver the liquid rinse 43 by gravity to the mouth of the inlet funnel 37. Preferably the tubing 47 is formed of a plastic material such as polyvinylchloride (e.g. Tygon tubing).

A rinse controlling valve 123 is positioned to control flow of the liquid rinse 43 through the tubing 47 from the rinse container 45 to the column 21. The rinse controlling valve 123 is located along the tubing 47 between the rinse container 45 and the column 21 and is coupled to the tubing to control the flow of rinse 43 through the tubing. The valve 123 may be any type of conventional valve which may be used for controlling liquid flow in tubing, but preferably the valve is a solenoid actuated valve that is normally closed so that the flow of rinse 43 from the rinse container 45 does not interfere with the flow of urine from the cage 13. The valve 123 may be manually activated by pressing a manual rinse switch 124 which is electrically connected to the valve 123 to control operation of the valve. Most preferably, the valve 123 is actuated and controlled by the data processing system 41, as described in further detail below.

Preferably, the system includes a data processing system 41. The data processing system receives, processes, stores, and prints data from the analyzing device 77 or measuring means and from the weighing means 107. The data processing system also may be used to control operation of the valves 39, 105, and 123 to automatically rinse the column 21 without interrupting collection of data on a series of urinary events and to temporarily suspend operation of the system 11 without terminating a long term test so the cage may be cleaned.

The data processing system 41 is comprised of a central processing unit 125 coupled in data communication with a storage device 127, preferably a fixed drive storage device. A user input device 129, such as a keyboard, may also be coupled to the central processing unit 125 so user commands may be entered to the central processing unit 125. A printer 130 is connected to the data processing system 41 so that accumulated data may be printed in hard copy. In a preferred embodiment, the data processing system 41 is coupled in data communication with a network 131 of remote data processing systems 133 so that information from the data processing system 41 may be communicated to and between the remote data processing systems 133. Most preferably, the data processing system 41 is a dedicated data acquisition and control system.

The data processing system 41 collects and stores data from the analyzing device 77 and from the weighing means 107. The analyzing device 77 and the weighing means 107 are coupled in data communication with the data processing system 41 so measurements made by the analyzing device 77 and the weighing means 107 are input to the data processing system 41. The data processing system 41 receives and stores the data in its storage device 127. Preferably, the meter 97 of the analyzing device and the scale 119 of the weighing means are coupled in data communication with the data processing system 41. In one embodiment of the invention, the data processing system monitors and stores data relating to the ion content of each urine sample, preferably the pH, the weight of each urine sample, the total weight of the series of urine samples, and the date and time of each urinary event.

Figure 6:
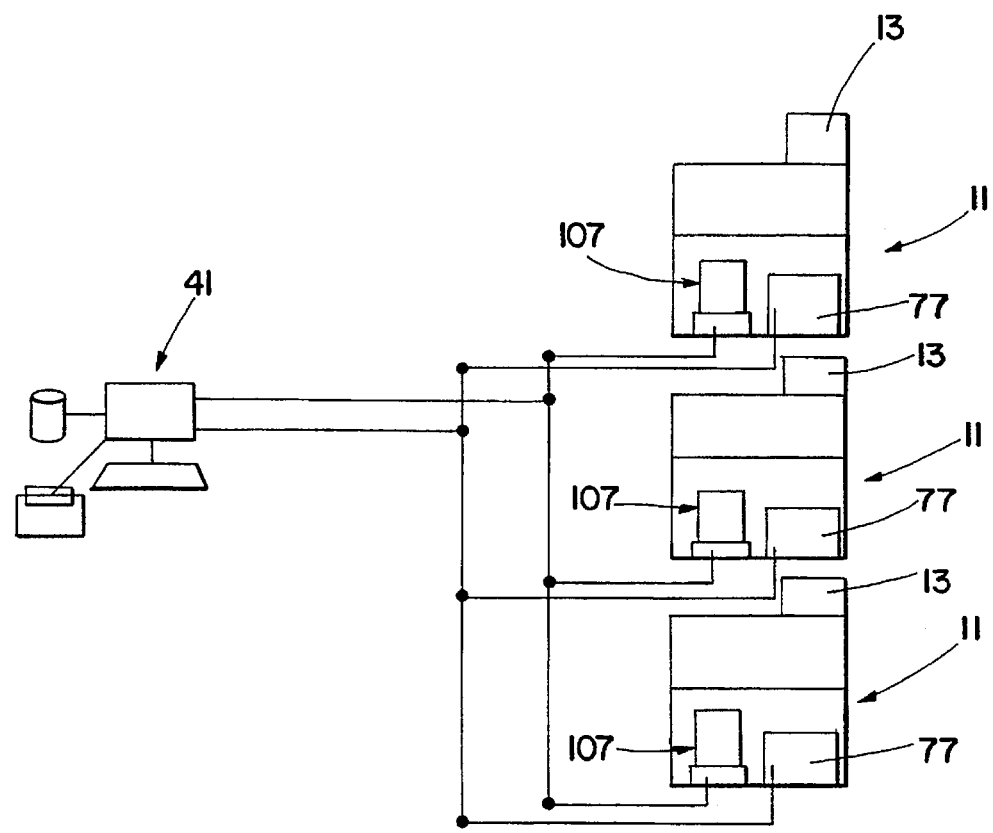
FIG. 6 is a schematic view of multiple animal urine analysis systems coupled in communication with a data processing system.

In another preferred embodiment of the invention, shown in FIG. 6, the data processing system monitors and stores the above data for a multiple number of systems 11 where each system 11 monitors an animal in a cage. The data processing system 41 is coupled in data communication with the analyzing device 77 and the weighing means 107 of each system 11 to receive and store data measured by each analyzing device and each weighing means. The data processing system also 41 monitors and stores data regarding the date, time, cage number, and animal identification number for each urinary event of each animal in the cages. The data processing system includes programming which may temporarily suspend receipt and storage of data from the analyzing device 77 and the weighing means 107 of a system 11 to permit cleaning of the system's cage without disrupting collection of data from the other systems.

Preferably, the data processing system 41 is also used to automatically control the rinsing of the column with liquid rinse 43. The data processing system may be used to initiate and control a rinse cycle after each urinary event and at predetermined time intervals regardless of whether a urinary event has occurred. The column 21 is rinsed to remove urine from the column so urine from a previous urinary event does not interfere with the measurement of urine from a subsequent urinary event; so that protein in the urine does not coat or clog the probe 85; and to maintain a fresh liquid solution about the probe 85.

To initiate a rinse cycle, the data processing system 41 determines whether a urinary event has occurred or whether a predetermined period of time has elapsed. The data processing system 41 determines whether a predetermined period of time has elapsed by determining when the time elapsed since the previous rinse cycle exceeds a preset adjustable time period. Preferably the preset time period is four hours so the column is rinsed at least every four hours.

The data processing system 41 determines when a urinary event has occurred by determining first when a urinary event is initiated and then determining when that urinary event ends. The data processing system 41 detects the initiation of a urinary event by a change beyond a threshold limit in the weight indicated by the weighing means 107. The data processing system then proceeds to determine when the urinary event has been completed by determining when the change in weight measured by the weighing means 107 has dropped to an insignificant amount, preferably by scanning input from the scale 119 every 20 seconds to determine whether the change in weight indicated by the scale has fallen below a threshold level.

The data processing system 41 is coupled in data communication with the urine controlling valve 39, the rinse controlling valve 123, and the three way valve 105 to control the flow of fluids through the system 11. Once the data processing system 41 has determined that a urinary event is complete or a predetermined period of time has elapsed, the valves 39, 105, and 123 are electronically actuated to permit liquid rinse 43 from the rinse container 45 to rinse the column 21. The urine controlling valve 39 is closed to prevent urine from another urinary event from entering the column. The rinse controlling valve 123 is opened to permit liquid rinse 43 to flow from the rinse container 45 to the column 21. The three way valve 105 is actuated to close outlet 113 to the container 117 so the rinse volume is not measured by the weighing means 107. Simultaneously the valve 105 is actuated to open the outlet 111 to the drain so liquid rinsed from the column 21 is directed to a drain.

The data processing system 41 maintains the valves 39, 105, and 123 in this rinse position for a predetermined period of time. The rinse valve 123 is opened for a period of time to permit a sufficient amount of liquid rinse 43 to flow to the column 21 to thoroughly rinse the column. In a preferred embodiment, the rinse valve 123 is opened for a period of six seconds. The three way valve 105 is switched to open outlet 111 to the drain and to close outlet 113 to the container 117 for a period of time sufficient to allow the entire volume of liquid 55 displaced from the column 21 by the liquid rinse 43 to flow into the drain outlet 111. In a preferred embodiment, the three way valve 105 is switched to the rinse position for a period of 24 seconds. The urine controlling valve 39 is closed during the period of time that the three way valve 105 is open. Further urination by the animal is trapped in the collection pan 31 and tubing 35 by the valve 39 so the urine is not added to the rinse 43 and is retained for measurement after the rinse cycle is complete. In a preferred embodiment the urine controlling valve 39 is closed for a period of 24 seconds after which the valve 39 is reopened to its normally open position.

After the rinse is complete, the data processing system controls the valves 39, 105, and 123 to place the valves back into position to collect urine in the column 21. The urine controlling valve 39 is opened to allow urine to flow from the cage 13 to the column 21, the rinse controlling valve 123 is closed to prevent flow of liquid rinse 43 from the rinse container 45 to the column, and the three way valve 105 is switched to open outlet 113 to allow liquid overflow from the column to flow to the container 117 while closing outlet 111 to the drain.

In a preferred embodiment, the system 11 is located in a system housing 135. As shown in FIG. 1, the housing 135 may be used to support various elements of the system. The housing is divided into sections 141 and 143 which hold the elements of the system 11 in proper position to utilize gravity so the system functions correctly. Preferably the housing 135 supports the column 21, the analyzing device 77, the weighing means 107, funnels 37 and 69, and the three way valve 105, and their elements. Particularly, the housing 135 includes a column support 137 which supports the elements of the column 21 and the inlet funnel 37, and a valve support 139 which supports three way valve 105 and the outlet funnel 69. The housing 135 may also include an electrical power switch 147 for controlling the power supply to the electrically powered elements of the system such as the analyzing device 77, the scale 119, and the valves 39, 105, and 123.

As shown in FIG. 5, in one embodiment the cage 13 in its cage support frame 14 is located in a movable frame 149 which may be located about a lift 145 which supports the housing 135. The movable frame has wheels 151 which enable the frame 149 to be rolled away from the housing 135 to permit easy access to the cage 13 so the cage may be regularly cleaned without moving the lift 145 or the housing 135. The movable frame 149 is positioned in front of the housing 135 and the lift 145 with the cage 13 extending over the front portion of the housing 135. The rinse container 45 is located on the rear portion of the housing 135 behind the cage.

The cage support frame 14 secures the cage 13 in the movable frame 149. As described above, the cage 13 is supported in the cage support frame 14. The cage support frame 14 is supported on rails 148 of the movable frame 149. Latches 153 retain the cage support frame on the rails 148. The latches 153 pivot about pivot pins 155 so the cage support frame 14 may be easily located on or removed from the rails 148, and may be secured on the rails 148 by pivoting the latches to a locking position(shown in solid lines).

The frame 149 locates the cage 13 over the housing 135 positioned to be coupled to the tubing 35 which is directed to the column. The movable frame 149 is located in front of the housing 135 and the lift 145 with the cage extending over the front portion of the housing 135. The collection pan 27 of the cage is removably located in the support rails 22 of the cage support frame 14 beneath the filter screen 25 and over the housing 135. The drain port 33 of the pan 27 is removably coupled to the tubing 35. The lift 145 may be used to adjust the height of the housing 135 relative to the cage in the frame 141 to facilitate coupling the tubing 35 to the cage. The pan 27 may be removed at regular intervals for cleaning by uncoupling the tubing 35 from the drain port and sliding the pan out of the rails.

In operation, referring again to FIG. 1, an animal is placed in the cage for monitoring. When the animal urinates, the mesh filter screens 23 and 25 filter the urine to remove feces, hair, food particles, or other solid impurities. The urine flows by gravity into the collection pan 27 which directs the urine through the drain port 33 into the tubing 35.

The tubing 35 directs the urine from the cage 13 to the column 21. The urine flows through the tubing 35 to the urine controlling valve 39. The valve 39 is maintained in an open position unless the column 21 is being rinsed so the urine normally flows through the valve. If the column 21 is being rinsed, the valve 39 halts the flow of the urine until the rinse is completed then allows the urine to flow to the column 21. The tubing 35 deposits the urine in the inlet funnel 37 which delivers the urine to the column.

The urine enters the column 21 from the inlet funnel 37 through the column inlet 53. The urine displaces the liquid in the column and is analyzed by the analyzing device 77. The analyzing device preferably analyzes the urine for its sodium ($Na^+$), potassium ($K^+$), hydrogen ($H^+$), calcium ($Ca^{2+}$), magnesium ($Mg^{2+}$), chloride ($Cl^-$), or phosphorus ion content, and most preferably for its hydrogen ion content (pH). Preferably the data determined by the analyzing device 77 is communicated to the data processing system 41 which automatically records the data.

The urine entering the column 21 displaces an equivalent volume of liquid 55 through the column outlet 61. The liquid displaced through the column outlet 61 flows into the outlet funnel 69 which directs the liquid into the three-way valve 105. The three-way valve 105 directs the liquid through outlet 113 into the tubing 115 which delivers the liquid to the weighing means 107 by gravity.

The container 117 of the weighing means 107 receives the liquid for weighing. The scale 119 of the weighing means 107 weighs the liquid to determine the weight of the corresponding volume of urine. The scale 119 is adjusted to compensate for the weight of the container 117 so the container's weight is not included in the determination of the liquid weight. Preferably the data determined by the weighing means 107 is communicated to the data processing system 41 which automatically records the data.

After the animal has completely urinated and the urine has been analyzed and its corresponding volume of liquid has been weighed, the column 21 is rinsed. Preferably the data processing system 41 determines when urine has been received and when the urinary event is complete by monitoring data from the scale 119. The column is rinsed by controlling the operation of the valves 39, 105 and 123 to allow flow of rinse 43 to the column while blocking the flow of further urine into the column, and to open flow of liquid from the column to a drain while blocking flow of liquid from the column to the weighing means 107. The valves 39, 105 and 123 may be operated manually using the manual rinse switch 124, however it is preferred that the data processing system automatically control operation of the valves.

Rinse 43 from the rinse container 45 flows by gravity through the tubing 47 and the rinse controlling valve 123 to the inlet funnel 37. The rinse 43 flows into the column inlet 53 from the inlet funnel 37 to join the trailing edge 65 of the liquid 55 in the column 21. The rinse 43 displaces liquid 55 through the column outlet 61 into the outlet funnel 69, through the three way valve 105, out the outlet 111 and into the drain tube 109 for disposal in a drain. A sufficient volume of rinse 43 is added to the column 21 to completely flush the column 21 of urine. After the rinse is complete, the valves are returned to a position blocking flow of rinse 43 to the column while allowing urine to flow to the column, and blocking flow of liquid from the column to the drain while allowing liquid flow to the weighing means.

The data processing system 41 also controls the valves 39, 105, and 123 to automatically rinse the column 21 after a predetermined period of time has elapsed, regardless of whether the animal in the cage 13 has urinated. The data processing system periodically measures the period of time elapsed since the last rinse cycle and compares the elapsed time with a predetermined rinse schedule time. If the elapsed time is greater than the predetermined rinse schedule time then the rinse cycle described above is automatically initiated by the data processing system 41.

The system 11 is preferably used to analyze and weigh each urination of a series of urinations from an animal in the cage 13. Urine is repetitively received in the column and analyzed with the analyzing device 77 for each urinary event of a series of urinary events. A volume of liquid is corresponding to the volume of received urine is repetitively discharged from the column 21 and weighed by the weighing means 107 for each respective urinary event of a series of urinary events. Preferably, data from the analyzing device 77 and the weighing means 107 is transmitted to the data processing system 41, which automatically records the data. The column is then automatically rinsed after the urine of each respective urination has been analyzed and weighed, or after a predetermined period of time has elapsed.

The above description is intended to be illustrative and not limiting. It will be readily apparent to one skilled in the art that numerous changes and modifications may be made to the invention as disclosed above within the scope of the invention.

What is claimed is:

1. An animal urine analysis system, comprising:
   a column structured and arranged to receive urine from an animal and to discharge a volume of liquid corresponding to the volume of received urine;
   measuring means engaged with said column for measuring a characteristic of said urine; and
   weighing means positioned to collect said volume of liquid discharged from said column, said weighing means weighing said volume of discharged liquid to determine a weight of the volume of urine corresponding to said volume of discharged liquid.

2. The animal urine analysis system of claim 1, wherein said column has an inlet for receiving urine, and outlet for discharging liquid and a U-shaped section located between said inlet and said outlet for capturing and retaining liquid in said column, said column having a constant-level volume of liquid therein.

3. The animal urine analysis system of claim 2, wherein said column is structured and arranged to maintain a trailing edge of the liquid in said column proximate to said column inlet, and said measuring means is engaged with said column proximate to said column inlet positioned to analyze urine added to said trailing edge of said liquid.

4. The animal urine analysis system of claim 2 wherein said column is structured and arranged to discharge a volume of said liquid in said column from said column outlet equivalent to a volume of liquid received in said column inlet, where said weighing means is positioned to receive said volume of liquid discharged from said column outlet.

5. The animal urine analysis system of claim 1 further comprising a cage for holding an animal, said cage having a fluid pervious floor through which urine from said animal will drain, said cage floor being structured and arranged to fluidly communicate with said column to immediately deliver fresh urine from said animal to said column for analysis by said measuring means.

6. The animal urine analysis system of claim 5 wherein said fluid pervious floor includes a filter for removing solid matter from said urine so that said urine is free of impurities.

7. The animal urine analysis system of claim 5 further comprising a rinse container having a liquid rinse therein, said rinse container being in fluid communication with said column to enable said liquid rinse to be dispensed from said rinse container to rinse said column.

8. The animal urine analysis system of claim 7 further comprising:
   a urine controlling valve positioned to control flow of said urine from said cage to said column;
   a rinse controlling valve positioned to control flow of rinse from said rinse container to said column; and
   a drain valve positioned to control flow of liquid from said column to either said weighing means or a drain;
   wherein said urine controlling valve and said rinse controlling valve cooperatively control flow of said liquid rinse and said urine to said column, and said drain valve controls flow of liquid discharged from said column, to permit said column to be rinsed while retaining urine from said animal and while maintaining a volume of liquid in said weighing means corresponding only to a volume of urine received from said animal.

9. The animal urine analysis system of claim 8 further comprising a data processing system coupled in data communication with said urine control valve, said rinse control valve, and said drain valve to automatically control operation of said valves to automatically rinse said column.

10. The animal urine analysis system of claim 1 further comprising a data processing system coupled in data communication with said measuring means and said weighing means for receiving and storing data from said measuring means and said weighing means.

11. The animal urine analysis system of claim 10 wherein said data processing system is coupled in data communication with said measuring means and said weighing means to receive and store data from said measuring means and said weighing means for each urination of a series of urinations from said animal.

12. The animal urine analysis system of claim 10 wherein said data processing system is structured to determine from data received from said weighing means when urine is intially received in said column from said animal and when receipt of urine from said animal is terminated.

13. The animal urine analysis system of claim 1 wherein said measuring means is a meter for measuring $Na^+$, $K^+$, $H^+$, $Ca^{2+}$, $Mg^{2+}$, $Cl^-$, or phosphorus content of urine received in said column.

14. The animal urine analysis system of claim 13 wherein said meter is a pH meter.

15. The animal urine analysis system of claim 1 wherein said weighing means comprises a scale and a container, where said container is positioned to receive liquid discharged from said column and is located on said scale so that liquid received in said container is weighed by said scale.

16. The animal urine analysis system of claim 15 wherein said container is removably located on said scale, said container being free of attachments so that said container may be freely removed from said scale.

17. An animal urine analysis system, comprising:
- a cage for holding an animal, said cage having a fluid pervious floor through which urine from said animal may drain;
- a column fluidly coupled to said cage floor for receiving each urination of a series of urinations from said animal in said cage, said column being structured and arranged to retain a constant-level volume of liquid therein and to discharge a volume of liquid corresponding to the volume of each urination received in said column;
- a rinse container having liquid rinse therein, said rinse container being fluidly coupled to said column for dispensing said liquid rinse to said column; an analytical device located proximate to said column positioned to analyze each urination received in said column; and
- weighing means positioned to collect said liquid discharged from said column, said weighing means weighing said discharged liquid to determine a weight of the volume of each urination received in said column.

18. The animal urine analysis of claim 17 wherein said column has an inlet for receiving urine, and outlet for discharging liquid and a U-shaped section located between said inlet and said outlet for capturing and retaining a constant-level volume of liquid in said column.

19. The animal urine analysis system of claim 18 wherein said column is structured and arranged to maintain a trailing edge of the liquid in said column proximate to said column inlet, and said analyzing device is engaged with said column proximate to said column inlet positioned to analyze urine added to said trailing edge of said liquid.

20. The animal urine analysis system of claim 18 wherein said column is structured and arranged to discharge a volume of said liquid in said column from said column outlet equivalent to a volume of liquid received in said column inlet, where said weighing means is positioned to receive said volume of liquid discharged from said column outlet.

21. The animal urine analysis system of claim 17 further comprising a data processing system coupled in data communication with said analyzing device and said weighing means for receiving and storing data from said analyzing device and said weighing means.

22. The animal urine analysis system of claim 21 wherein said data processing system is structured to determine from data received from said weighing means when urine is intially received in said column from said animal and when receipt of urine from said animal in said column is terminated for each urination of said series of urinations.

23. The animal urine analysis system of claim 21 wherein said data processing system is structured to temporarily suspend receipt and storage of data from said analyzing device and said weighing means so said cage may be cleaned without interrupting analysis of each urination of said series of urinations.

24. The animal urine analysis system of claim 21 further comprising:
- a urine controlling valve positioned to control flow of said urine from said cage to said column, said data processing system being coupled in data communication with said urine controlling valve to automatically control operation of said urine controlling valve;
- a rinse controlling valve positioned to control flow of rinse from said rinse container to said column, said data processing system being coupled in data communication with said rinse controlling valve to automatically control operation of said rinse controlling valve; and
- a drain valve positioned to control flow of liquid discharged from said column to either said weighing means or a drain, said data processing system being coupled in data communication with said drain valve to automatically control operation of said drain valve.

25. The animal urine analysis system of claim 17 wherein said analyzing device is a meter for measuring $Na^+$, $K^+$, $H^+$, $Ca^{2+}$, $Mg^{2+}$, $Cl^-$, or phosphorus content of urine received in said column.

26. The animal urine analysis system of claim 25 wherein said meter is a pH meter.

27. The animal urine analysis system of claim 17 wherein said weighing means comprises a scale and a container, where said container is positioned to receive liquid discharged from said column and is located on said scale so that liquid received in said container is weighed by said scale.

28. The animal urine analysis system of claim 27 wherein said container is removably located on said scale, said container being free of attachments so that said container may be freely removed from said scale.

29. An animal urine analysis system, comprising:
- a plurality of cages for holding a plurality of animals, where each cage holds a respective animal for testing, each cage having a fluid pervious floor through which urine from an animal may drain;
- a plurality of columns, each column being fluidly coupled to a fluid pervious floor of a respective cage for receiving each urination of a series of urinations from an animal in said respective cage, where each column is structured and arranged to retain a constant-level volume of liquid therein and to discharge a volume of liquid corresponding to the volume of each urination received from an animal;
- a plurality of analytical devices, each analytical device being located proximate to a respective column positioned to analyze each urination received in said respective column;
- a plurality of weighing means, each weighing means being positioned to collect liquid discharged from a respective column, each weighing means weighing liquid discharged from its respective column to determine a weight of the volume of each urination received in its respective column; and
- a data processing system coupled in data communication with each analyzing device and each weighing means for receiving and storing data from each analyzing device and each weighing means for each urination of a series of urinations from each animal in said cages.

30. The animal urine analysis system of claim 29, wherein said data processing system is structured to temporarily suspend receipt and storage of data from each respective analyzing device and weighing means so each cage may be individually cleaned without disrupting collection of data from said plurality of cages.

31. The animal urine analysis system of claim 29 further comprising a plurality of rinse containers having liquid rinse therein, each rinse container being fluidly coupled to a respective column for dispensing liquid rinse to said respective column.

32. A method of analyzing urine from an animal, comprising:
   a.) receiving urine into a column directly from an animal in a cage and analyzing said urine in said column with an analytical device; and
   b.) discharging a volume of liquid from said column corresponding to the volume of said urine and weighing said liquid discharged from said column to determine the weight of said volume of urine.

33. The method of analyzing urine from an animal of claim 32, further comprising automatically rinsing said column with a liquid rinse after analyzing said urine in said column and weighing said liquid discharged from said column.

34. The method of analyzing urine from an animal of claim 32, further comprising automatically rinsing said column with a liquid rinse after a predetermined period of time has elapsed.

35. The method of analyzing urine from an animal of claim 32, further comprising automatically recording data determined by weighing said discharged liquid and by analyzing said urine with said analytical device.

36. The method of analyzing urine from an animal of claim 32, wherein said urine is analyzed for $Na^+$, $K^+$, $H^+$, $Ca^{2+}$, $Mg^{2+}$, or $Cl^-$ or phosphorus content.

37. A method of analyzing each urination of a series of urinations from an animal, comprising:
   a.) receiving urine into a column directly from said animal in a cage for each urination of said series of urinations from said animal and discharging a volume of liquid from said column corresponding to a volume of urine received into said column;
   b.) analyzing said received urine with an analytical device, and weighing said discharged volume of liquid to determine the weight of said volume of said received urine; and
   c.) repeating steps a.) and b.) for each urination of said series of urinations.

38. The method of analyzing each urination from a series of urinations from an animal of claim 37, further comprising automatically rinsing said column with a liquid rinse after each urination once said urine has been analyzed with said analyzing device and said volume of discharged liquid has been weighed.

39. The method of analyzing each urination of a series of urinations from an animal of claim 37, further comprising automatically rinsing said column with a liquid rinse after a predetermined time regardless whether a urination has occurred.

40. The method of analyzing each urination of a series of urinations from an animal of claim 37, further comprising automatically storing data determined by analyzing said urine and weighing said liquid discharged from said column for each urination of said series of urinations.

* * * * *